United States Patent
Cotter

(10) Patent No.: US 11,040,188 B2
(45) Date of Patent: *Jun. 22, 2021

(54) FLOW ESTIMATION USING HALL-EFFECT SENSORS AND/OR MAGNETIC BEARING CURRENTS

(71) Applicant: TC1 LLC, St. Paul, MN (US)

(72) Inventor: Christopher J. Cotter, Newburyport, MA (US)

(73) Assignee: TC1 LLC, St. Paul, MN (US)

( * ) Notice: Subject to any disclaimer, the term of this patent is extended or adjusted under 35 U.S.C. 154(b) by 126 days.

This patent is subject to a terminal disclaimer.

(21) Appl. No.: 16/382,686

(22) Filed: Apr. 12, 2019

(65) Prior Publication Data

US 2019/0231954 A1 Aug. 1, 2019

Related U.S. Application Data

(63) Continuation of application No. 15/873,427, filed on Jan. 17, 2018, now Pat. No. 10,300,184, which is a
(Continued)

(51) Int. Cl.
*A61M 1/12* (2006.01)
*A61M 60/50* (2021.01)
(Continued)

(52) U.S. Cl.
CPC .......... *A61M 60/50* (2021.01); *A61M 60/419* (2021.01); *A61M 60/148* (2021.01);
(Continued)

(58) Field of Classification Search
None
See application file for complete search history.

(56) References Cited

U.S. PATENT DOCUMENTS 5,695,471 A 12/1997 Wampler
5,708,346 A 1/1998 Schob
(Continued)

FOREIGN PATENT DOCUMENTS

EP 1 812 094 8/2007
EP 3 164 168 A2 5/2017
(Continued)

OTHER PUBLICATIONS

Khare, Aditi, Estimation and Control of the Pump Pressure Rise and Flow from Intrinsic Parameters for a Magnetically-Levitated Axial Blood Pump, Rochester Institute of Technology, 2009, UMP Microform 1460273, ProQuest LLC, pp. 1-124. (Year: 2009).*

*Primary Examiner* — Kennedy Schaetzle
(74) *Attorney, Agent, or Firm* — Kilpatrick Townsend & Stockton LLP

(57) ABSTRACT

Methods and apparatus for estimating flow rate in a blood circulation assist system employing impeller eccentricity. A method includes magnetically rotating an impeller within a blood flow channel of a blood pump. The impeller is levitated within the blood flow channel transverse to the impeller axis of rotation. A rotational speed for the impeller is determined. At least one impeller transverse position parameter is determined. The at least one impeller transverse position parameter is based on at least one of (1) an amount of a bearing current that is used to levitate the impeller transverse to the impeller axis of rotation, and (2) a position of the impeller within the blood flow channel transverse to the impeller axis of rotation. A flow rate of blood pumped by the blood pump is estimated based on the impeller rotational speed and the at least one impeller transverse position parameter.

19 Claims, 14 Drawing Sheets

Related U.S. Application Data continuation of application No. 15/214,099, filed on Jul. 19, 2016, now Pat. No. 9,901,666.

(60) Provisional application No. 62/194,608, filed on Jul. 20, 2015.

(51) Int. Cl.
*A61M 60/419* (2021.01)
*A61M 60/82* (2021.01)
*A61M 60/148* (2021.01)
*A61M 60/205* (2021.01)
*A61M 60/422* (2021.01)
*A61M 60/562* (2021.01)

(52) U.S. Cl.
CPC ......... *A61M 60/205* (2021.01); *A61M 60/422* (2021.01); *A61M 60/562* (2021.01); *A61M 60/82* (2021.01); *A61M 2205/3317* (2013.01); *A61M 2205/3334* (2013.01); *A61M 2205/3365* (2013.01); *A61M 2205/8212* (2013.01)

(56) References Cited

U.S. PATENT DOCUMENTS

| | | | |
|---|---|---|---|
| 5,725,357 A | 3/1998 | Nakazeki et al. | |
| 5,888,242 A | 3/1999 | Antaki et al. | |
| 5,947,703 A | 9/1999 | Nojiri et al. | |
| 5,951,263 A | 9/1999 | Taylor et al. | |
| 6,053,705 A | 4/2000 | Schob et al. | |
| 6,071,093 A | 6/2000 | Hart | |
| 6,100,618 A | 8/2000 | Schoeb et al. | |
| 6,116,862 A | 9/2000 | Rau et al. | |
| 6,135,943 A | 10/2000 | Yu et al. | |
| 6,149,683 A * | 11/2000 | Lancisi | A61M 60/82 623/3.1 |
| 6,176,822 B1 | 1/2001 | Nix et al. | |
| 6,186,665 B1 | 2/2001 | Maher et al. | |
| 6,222,290 B1 | 4/2001 | Schob et al. | |
| 6,234,772 B1 | 5/2001 | Wampler et al. | |
| 6,249,067 B1 | 6/2001 | Schob et al. | |
| 6,264,635 B1 | 7/2001 | Wampler et al. | |
| 6,278,251 B1 | 8/2001 | Schob | |
| 6,351,048 B1 | 2/2002 | Schob et al. | |
| 6,355,998 B1 | 3/2002 | Schoeb et al. | |
| 6,468,041 B2 | 10/2002 | Ozaki | |
| 6,575,717 B2 | 6/2003 | Ozaki et al. | |
| 6,589,030 B2 | 7/2003 | Ozaki | |
| 6,605,032 B2 | 8/2003 | Benkowski et al. | |
| 6,626,644 B2 | 9/2003 | Ozaki | |
| 6,634,224 B1 | 10/2003 | Schob et al. | |
| 6,688,861 B2 | 2/2004 | Wampler | |
| 6,707,200 B2 | 3/2004 | Carroll et al. | |
| 6,817,836 B2 | 11/2004 | Nose et al. | |
| 6,879,074 B2 | 4/2005 | Amrhein et al. | |
| 6,949,066 B2 | 9/2005 | Bearnson et al. | |
| 6,991,595 B2 | 1/2006 | Burke et al. | |
| 7,112,903 B1 | 9/2006 | Schob | |
| 7,138,776 B1 | 11/2006 | Gauthier et al. | |
| 7,150,711 B2 | 12/2006 | Nusser et al. | |
| 7,229,474 B2 | 6/2007 | Hoffmann et al. | |
| 7,239,098 B2 | 7/2007 | Masino | |
| 7,284,956 B2 | 10/2007 | Nose et al. | |
| 7,462,019 B1 | 12/2008 | Allarie et al. | |
| 7,497,116 B2 | 3/2009 | Miyakoshi et al. | |
| 7,511,443 B2 | 3/2009 | Townsend et al. | |
| 7,591,777 B2 | 9/2009 | LaRose | |
| 7,645,225 B2 | 1/2010 | Medvedev et al. | |
| 7,699,586 B2 | 4/2010 | LaRose et al. | |
| 7,699,588 B2 | 4/2010 | Mendler | |
| 7,854,631 B2 | 12/2010 | Townsendl et al. | |
| 7,861,582 B2 | 1/2011 | Miyakoshi et al. | |
| 7,887,479 B2 | 2/2011 | LaRose et al. | |
| 7,951,062 B2 | 5/2011 | Morello | |
| 7,976,271 B2 | 7/2011 | LaRose et al. | |
| 7,997,854 B2 | 8/2011 | LaRose et al. | |
| 8,007,254 B2 | 8/2011 | LaRose et al. | |
| 8,152,493 B2 | 4/2012 | LaRose et al. | |
| 8,157,720 B2 | 4/2012 | Marseille et al. | |
| 8,303,482 B2 | 11/2012 | Schima et al. | |
| 8,323,174 B2 | 12/2012 | Jeevanandam et al. | |
| 8,382,830 B2 | 2/2013 | Maher et al. | |
| 8,449,444 B2 | 5/2013 | Poirier | |
| 8,506,470 B2 | 8/2013 | LaRose et al. | |
| 8,506,471 B2 | 8/2013 | Bourque | |
| 8,517,699 B2 | 8/2013 | Horvath | |
| 8,556,795 B2 | 10/2013 | Bolyard et al. | |
| 8,562,508 B2 | 10/2013 | Dague et al. | |
| 8,597,350 B2 | 12/2013 | Rudser et al. | |
| 8,652,024 B1 | 2/2014 | Yanai et al. | |
| 8,657,733 B2 | 2/2014 | Ayre et al. | |
| 8,668,473 B2 | 3/2014 | LaRose et al. | |
| 8,764,621 B2 | 7/2014 | Badstibner et al. | |
| 8,870,739 B2 | 10/2014 | LaRose et al. | |
| 8,882,477 B2 | 11/2014 | Fritz, IV et al. | |
| 8,897,873 B2 | 11/2014 | Schima et al. | |
| 8,956,275 B2 | 2/2015 | Bolyard et al. | |
| 9,265,870 B2 | 2/2016 | Reichenbach et al. | |
| 9,511,179 B2 | 12/2016 | Casas et al. | |
| 9,901,666 B2 | 2/2018 | Cotter | |
| 10,300,184 B2 | 5/2019 | Cotter | |
| 2001/0031210 A1 | 10/2001 | Antaki et al. | |
| 2003/0163019 A1 | 8/2003 | Goldowsky | |
| 2003/0223879 A1 | 12/2003 | Yanai et al. | |
| 2004/0228724 A1 | 11/2004 | Capone et al. | |
| 2004/0241019 A1 | 12/2004 | Goldowsky | |
| 2005/0071001 A1 | 3/2005 | Jarvik | |
| 2005/0196293 A1 * | 9/2005 | Ayre | A61M 60/422 417/353 |
| 2005/0267322 A1 * | 12/2005 | LaRose | A61M 60/205 600/16 |
| 2007/0078293 A1 | 4/2007 | Shambaugh, Jr. et al. | |
| 2008/0021394 A1 | 1/2008 | LaRose et al. | |
| 2009/0203957 A1 | 8/2009 | LaRose et al. | |
| 2010/0130809 A1 | 5/2010 | Morello | |
| 2010/0241223 A1 | 9/2010 | Lee et al. | |
| 2010/0327687 A1 | 12/2010 | Iannello et al. | |
| 2011/0071337 A1 | 3/2011 | Thompson et al. | |
| 2011/0237863 A1 | 9/2011 | Ricci et al. | |
| 2011/0243759 A1 | 10/2011 | Ozaki et al. | |
| 2011/0313237 A1 | 12/2011 | Miyakoshi et al. | |
| 2012/0046514 A1 | 2/2012 | Bourque | |
| 2012/0095281 A1 | 4/2012 | Reichenbach et al. | |
| 2012/0226097 A1 | 9/2012 | Smith et al. | |
| 2012/0245681 A1 | 9/2012 | Casas et al. | |
| 2013/0030240 A1 | 1/2013 | Schima et al. | |
| 2013/0096364 A1 | 4/2013 | Reichenbach et al. | |
| 2013/0121821 A1 | 5/2013 | Ozaki et al. | |
| 2013/0127253 A1 | 5/2013 | Stark et al. | |
| 2013/0170970 A1 | 7/2013 | Ozaki et al. | |
| 2013/0225909 A1 | 8/2013 | Dormanen et al. | |
| 2013/0314047 A1 | 11/2013 | Eagle et al. | |
| 2013/0331934 A1 | 12/2013 | Kabir et al. | |
| 2014/0100413 A1 | 4/2014 | Casas et al. | |
| 2014/0194985 A1 | 7/2014 | Vadala, Jr. | |
| 2014/0275723 A1 | 9/2014 | Fritz, IV et al. | |
| 2014/0303426 A1 | 10/2014 | Kerkhoffs et al. | |
| 2014/0357937 A1 | 12/2014 | Reyes et al. | |
| 2015/0051438 A1 | 2/2015 | Taskin | |
| 2015/0367048 A1 | 12/2015 | Brown et al. | |
| 2016/0144092 A1 | 5/2016 | Casas et al. | |
| 2016/0235898 A1 | 8/2016 | Yanai et al. | |
| 2017/0021070 A1 | 1/2017 | Petersen | |
| 2017/0021071 A1 | 1/2017 | Cotter | |
| 2018/0140760 A1 | 5/2018 | Cotter | |

FOREIGN PATENT DOCUMENTS

| | | |
|---|---|---|
| WO | 2004017818 A2 | 3/2004 |
| WO | 2006055745 A2 | 5/2006 |
| WO | 2016001284 A2 | 1/2016 |

* cited by examiner

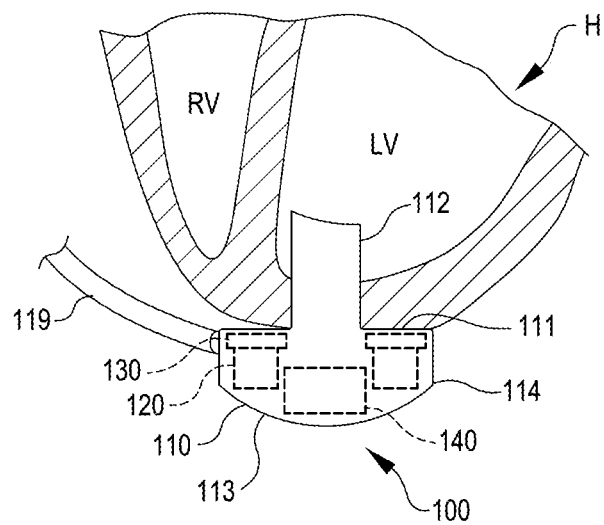
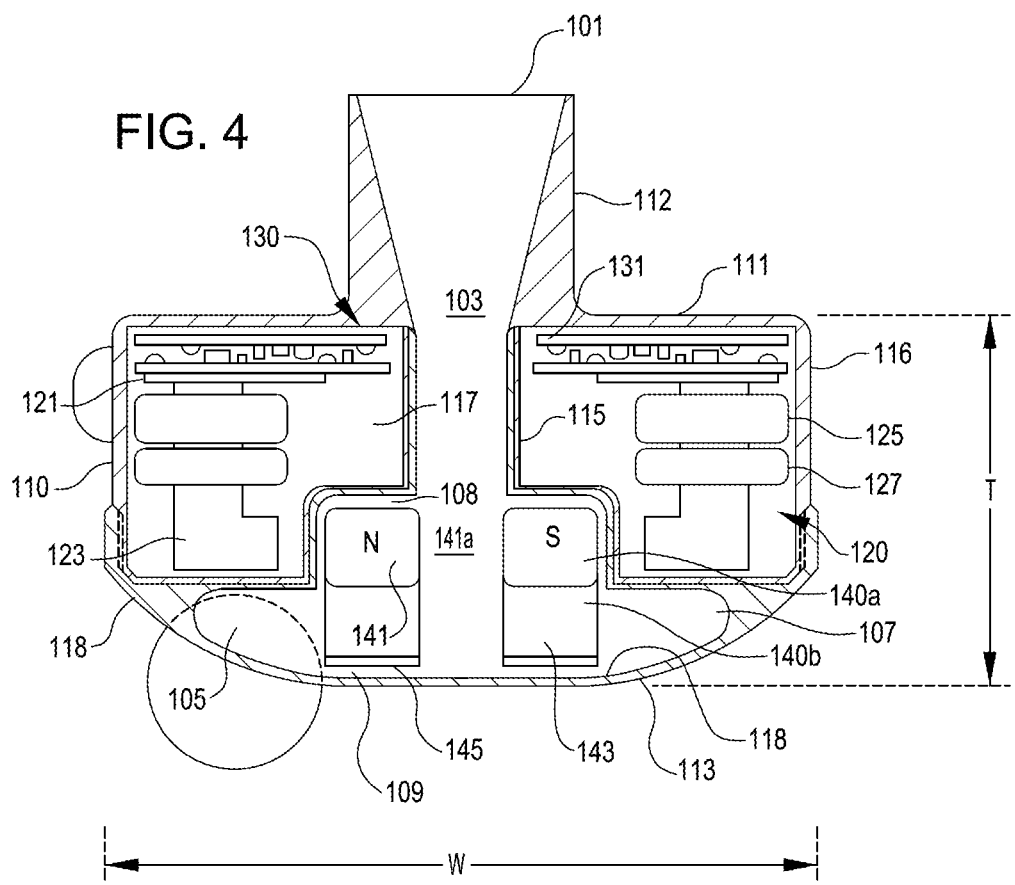

7000 rpm, 10 L/min 7000 rpm, 7 L/min

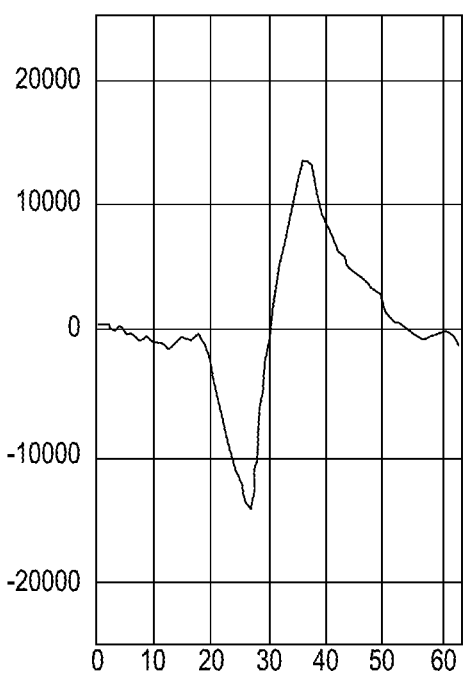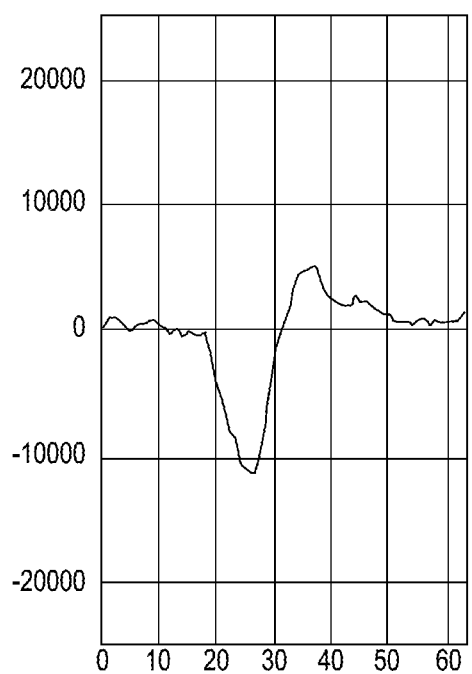
FIG. 20
7000 rpm, 3 L/min

FLOW ESTIMATION USING HALL-EFFECT SENSORS AND/OR MAGNETIC BEARING CURRENTS

CROSS-REFERENCES TO RELATED APPLICATIONS

The present application is a Continuation of U.S. Ser. No. 15/873,427 filed Jan. 17, 2018 (Allowed); which is a Continuation of U.S. Ser. No. 15/214,099 filed Jul. 19, 2016 (now U.S. Pat. No. 9,901,666); which claims priority to, and the benefit of, U.S. Provisional Appln No. 62/194,608 filed Jul. 20, 2015; the contents of which are incorporated herein by reference in their entirety for all purposes.

BACKGROUND

Ventricular assist devices, known as VADs, often include an implantable blood pump and are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function.

The flow rate of blood pumped by a VAD is an important parameter for both control of the blood pump and for informing a health care professional regarding the level of circulatory support provided to the patient by the VAD. Direct blood flow rate measurement, however, may be undesirable with respect to additional components, such a flow rate sensor, that would be used to directly measure the flow rate of blood pumped by the VAD. Such additional components may add to the complexity and size of the VAD, thereby potentially making the VAD more expensive and occupy more space within the patient. Additionally, a flow rate sensor may increase the rate of thrombosis (blood clot formation) as a result of the interface between the flow rate sensor and the blood flow.

In view of the challenges associated with direct blood flow rate measurement in a VAD, flow rate in a VAD may be estimated. For example, the blood flow rate in a VAD can be estimated based on the amount of electrical power consumed by the VAD. For some operational regimes of a blood pump, however, estimated flow rate based on electrical power consumed by the VAD may not be sufficiently accurate. As such, improved approaches for estimating blood flow rate in a VAD are desirable.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Improved methods for estimating blood flow rate in a blood circulation assist system include determining an impeller position parameter. In certain operating regimes of a blood pump, the impeller position parameter and impeller rotational speed are used to estimate the blood flow rate, thereby more accurately estimating the blood flow rate as opposed to estimating the blood flow rate based solely on impeller rotational rate and electrical power consumed by the blood pump.

Thus, in one aspect, a blood circulation assist system is provided that estimates the flow rate of blood pumped based in part on impeller position. The system includes a blood pump and a controller operatively coupled with the blood pump. The blood pump includes an impeller disposed within a blood flow channel of the blood pump and a motor stator operable to magnetically rotate the impeller. The impeller has an impeller axis of rotation around which the impeller is rotated. The motor stator is operable to magnetically levitate the impeller within the blood flow channel transverse to the impeller axis of rotation. The controller is configured to determine an impeller rotational speed for the impeller, determine an amount of a drive current used to rotate the impeller, and determine at least one impeller transverse position parameter. The at least one impeller transverse position parameter is based on at least one of (1) an amount of a bearing current that is used to levitate the impeller transverse to the impeller axis of rotation, and (2) a position of the impeller within the blood flow channel transverse to the impeller axis of rotation. The controller is configured to estimate a flow rate of blood pumped by the blood pump based on the impeller rotational speed and the drive current when the drive current is below a first drive current threshold. The controller is configured to estimate the flow rate based on the impeller rotational speed and the at least one impeller transverse position parameter when the drive current is above the first drive current threshold.

In some or all operating regimes of the blood pump, the controller can estimate the flow rate based on the impeller rotational speed, the drive current, and the at least one impeller position parameter. For example, the controller can be configured to estimate the flow rate based on the impeller rotational speed, the drive current, and the at least one impeller transverse position parameter when the drive current is between a second drive current threshold and a third drive current threshold.

Any suitable approach can be used to determine the first drive current threshold. In many embodiments, the first drive current threshold varies based on the impeller rotational speed. In many embodiments, the first drive current threshold is based on characteristics of variation in the amount of bearing current used to levitate the impeller transverse to the impeller axis of rotation in response to variation in the impeller rotational speed. For example, the first drive current threshold can be selected such that the amount of bearing current used to levitate the impeller transverse to the impeller axis increases in response to a decrease in the impeller rotational speed for drive currents above the first drive current threshold.

In many embodiments, the impeller impels the blood centrifugally and the blood pumped by the blood pump is output in a direction transverse to the impeller axis of rotation. In such embodiments, the non-symmetric nature of the blood flow output induces eccentricity in the transverse position of the impeller that varies with respect to the flow rate of the blood pumped. The at least one impeller transverse position parameter can be indicative of an amount of eccentricity of the impeller within the blood flow channel.

Any suitable approach can be used to determine the at least one impeller transverse position parameter. In many embodiments, the system can include at least one sensor generating output indicative of the position of the impeller within the blood flow channel transverse to the impeller axis of rotation. For example, the at least one sensor can include a plurality of hall sensors generating output indicative of magnetic flux levels of the motor stator that are indicative of the position of the impeller within the blood flow channel transverse to the impeller axis of rotation.

In many embodiments, the controller operates the blood pump to substantially minimize power consumption. For example, the controller can be configured to control the amount of a bearing current that is used to levitate the impeller transverse to the impeller axis of rotation so as to substantially minimize power consumption of the blood pump. In many embodiments, the controller is configured to control eccentricity of the impeller within the blood flow channel so as to substantially minimize power consumption of the blood pump. In many embodiments, the flow rate is estimated based on a target or measured eccentricity of the impeller within the blood flow channel when the drive current is above the first drive current threshold.

In many embodiments, the controller is configured to estimate a pressure differential across the impeller based on the at least one impeller transverse position parameter. For example, the pressure differential can be a function an off-center position for the impeller to minimize bearing current.

In another aspect, a method is provided for estimating blood flow rate in a blood circulation assist system. The method includes magnetically rotating an impeller around an impeller axis of rotation within a blood flow channel of a blood pump. The impeller is magnetically levitated within the blood flow channel transverse to the impeller axis of rotation. A controller operatively coupled with the blood pump determines an impeller rotational speed for the impeller. The controller determines at least one impeller transverse position parameter. The at least one impeller transverse position parameter is based on at least one of (1) an amount of a bearing current that is used to levitate the impeller transverse to the impeller axis of rotation, and (2) a target or measured position of the impeller within the blood flow channel transverse to the impeller axis of rotation. The controller estimates a flow rate of blood pumped by the blood pump based on the impeller rotational speed and the at least one impeller transverse position parameter.

In many embodiments, the method further includes estimating flow rate for some operating regimes based on a drive current used to rotate the impeller. For example, the controller can determine an amount of a drive current used to rotate the impeller. The controller can estimate a flow rate of blood pumped by the blood pump based on the impeller rotational speed and the drive current. In many embodiments, the flow rate is estimated: (1) based on the impeller rotational speed and the drive current when the drive current is below a first drive current threshold, and (2) based on the impeller rotational speed and the at least one impeller transverse position parameter when the drive current is above the first drive current threshold.

The first drive current can be determined using any suitable approach. For example, the method can include selecting the first drive current such that the amount of bearing current used to levitate the impeller transverse to the impeller axis increases in response to a decrease in the impeller rotational speed for drive currents above the first drive current threshold.

In some or all operating regimes of the blood pump, the method can estimate the flow rate based on the impeller rotational speed, the drive current, and the at least one impeller transverse position parameter. For example, the method can include determining, with the controller, an amount of a drive current used to rotate the impeller. The controller can estimate the flow rate based on the impeller rotational speed, the drive current, and the at least one impeller transverse position parameter when the drive current is between a second drive current threshold and a third drive current threshold.

In many embodiments of the method, the blood pump is controlled to substantially minimize power consumption of the blood pump. For example, the method can include controlling the amount of the bearing current used to levitate the impeller transverse to the impeller axis of rotation so as to substantially minimize power consumption of the blood pump.

In many embodiments of the method, the blood pump is configured and operated so that the transverse position of the impeller within the blood flow channel varies as a function of flow rate of the blood pump for at least a range of blood flow rates. For example, in many embodiments of the method, the blood pump is configured such that the impeller impels the blood centrifugally and the blood pumped by the blood pump is output in a direction transverse to the impeller axis of rotation.

Any suitable approach can be used to determine the at least one impeller transverse position parameter used to estimate flow rate. For example, the method can include processing, with the controller, output from a plurality of hall sensors indicative of magnetic flux levels used to levitate the impeller within the blood flow channel to determine eccentricity of the impeller within the blood flow channel. In many embodiments, the at least one impeller transverse position parameter is indicative of the determined eccentricity or a target eccentricity.

In many embodiments, the method includes estimating, with the controller, a pressure differential across the impeller based on the at least one impeller transverse position parameter. For example, the controller can estimate the pressure differential across the impeller based on an off-center position for the impeller to minimize bearing current.

For a fuller understanding of the nature and advantages of the present invention, reference should be made to the ensuing detailed description and accompanying drawings.

BRIEF DESCRIPTION OF THE DRAWINGS

FIG. 3 is an illustration of a blood pump in an operational position implanted in a patient's body.

FIG. 4 is a cross-sectional view of the blood pump of FIG. 3.

FIG. 20 is a plot showing bearing current variations during pulsatile mode operation of the example blood pump of FIG. 14 operated at a nominal 7000 rpm and 3 L/min.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
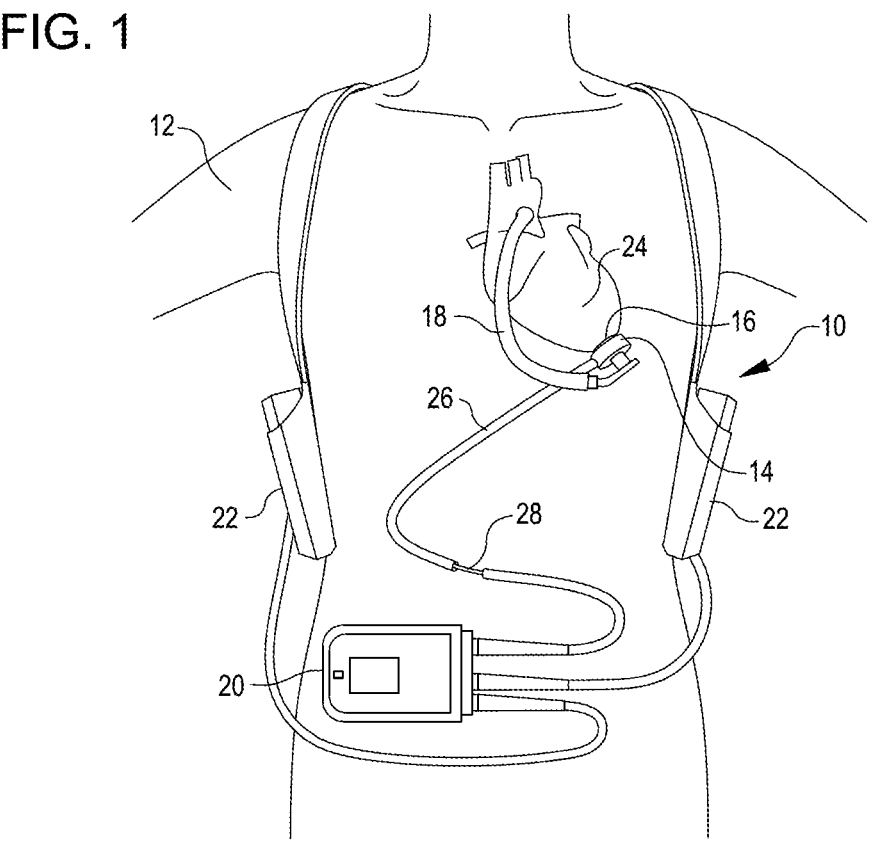
FIG. 1 is an illustration of a mechanical circulatory support system implanted in a patient's body, in accordance with many embodiments.
Figure 2:
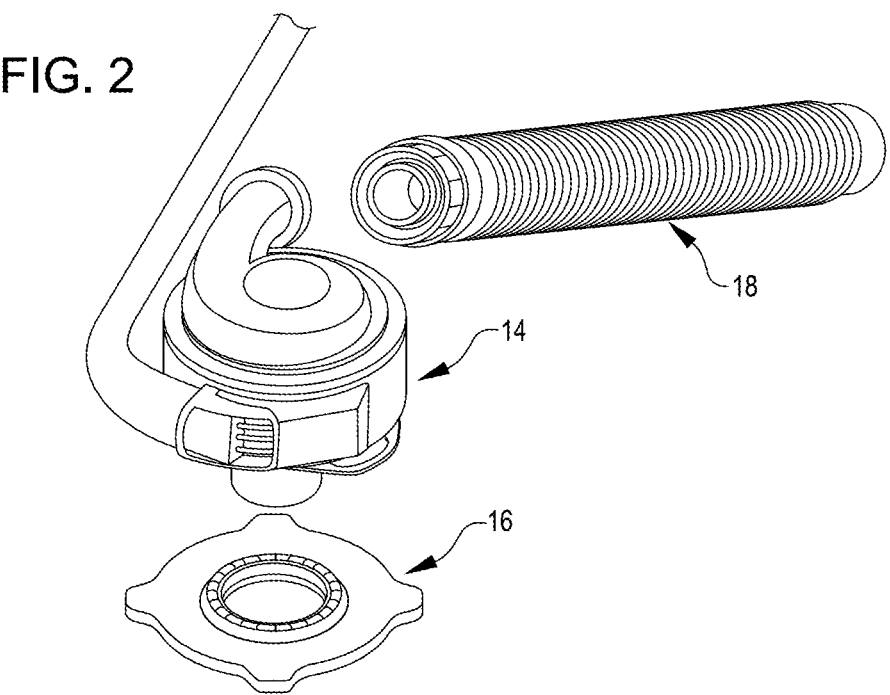
FIG. 2 is an exploded view of certain components of the circulatory support system of FIG. 1.

Referring now to the drawings, in which like reference numerals represent like parts throughout the several views, FIG. 1 is an illustration of a mechanical circulatory support system 10 implanted in a patient's body 12. The mechanical circulatory support system 10 includes an implantable blood pump assembly 14, a ventricular cuff 16, an outflow cannula 18, an external system controller 20, and power sources 22. The implantable blood pump assembly 14 can include a VAD that is attached to an apex of the left ventricle, as illustrated, or the right ventricle, or both ventricles of the heart 24. The VAD can include a centrifugal pump (as shown) that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIGS. 1 and 2, the blood pump assembly 14 can be attached to the heart 24 via the ventricular cuff 16, which can be sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation through the rest of the patient's vascular system.

FIG. 1 illustrates the mechanical circulatory support system 10 during battery 22 powered operation. A driveline 26 that exits through the patient's abdomen 28 connects the implanted blood pump assembly 14 to the external system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system 10 can be powered by either one, two, or more batteries 22. It will be appreciated that although the system controller 20 and power source 22 are illustrated outside/external to the patient body, the driveline 26, the system controller 20 and/or the power source 22 can be partially or fully implantable within the patient, as separate components or integrated with the blood pump assembly 14. Examples of such modifications are further described in U.S. Pat. No. 8,562,508 and U.S. Patent Publication No. 2013/0127253, all of which are incorporated herein by reference for all purposes in their entirety.

Figure 5:
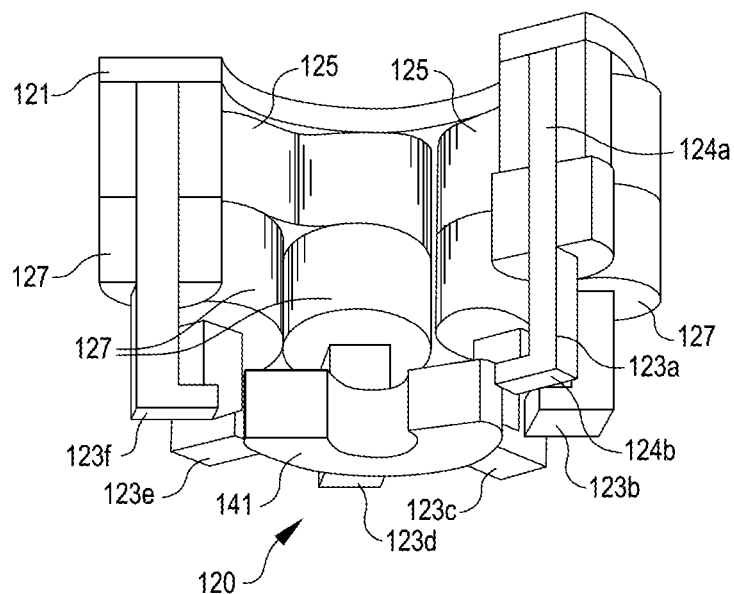
FIG. 5 is a partial cut-away perspective view of a stator of a blood pump.

With reference to FIGS. 3 to 5, a left ventricular assist blood pump assembly 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump assembly 100, such as the patient's diaphragm. To construct the illustrated shape of the puck-shaped housing 110 in a compact form, a stator 120 and electronics 130 of the pump assembly 100 are positioned on the inflow side of the housing toward first face 111, and a rotor 140 of the pump assembly 100 is positioned along the second face 113. This positioning of the stator 120, electronics 130, and rotor 140 permits the edge 114 to be chamfered along the contour of the rotor 140, as illustrated in at least FIGS. 2-4, for example.

Referring to FIG. 4, the blood pump assembly 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 4 and 5, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a can also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 can include one or more Hall sensors that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 can be adjusted, e.g., the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 can be approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the one or more Hall sensors may sense a current position of the rotor 140 and/or the permanent magnet 141, wherein the output voltage of the one or more Hall sensors may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 6:
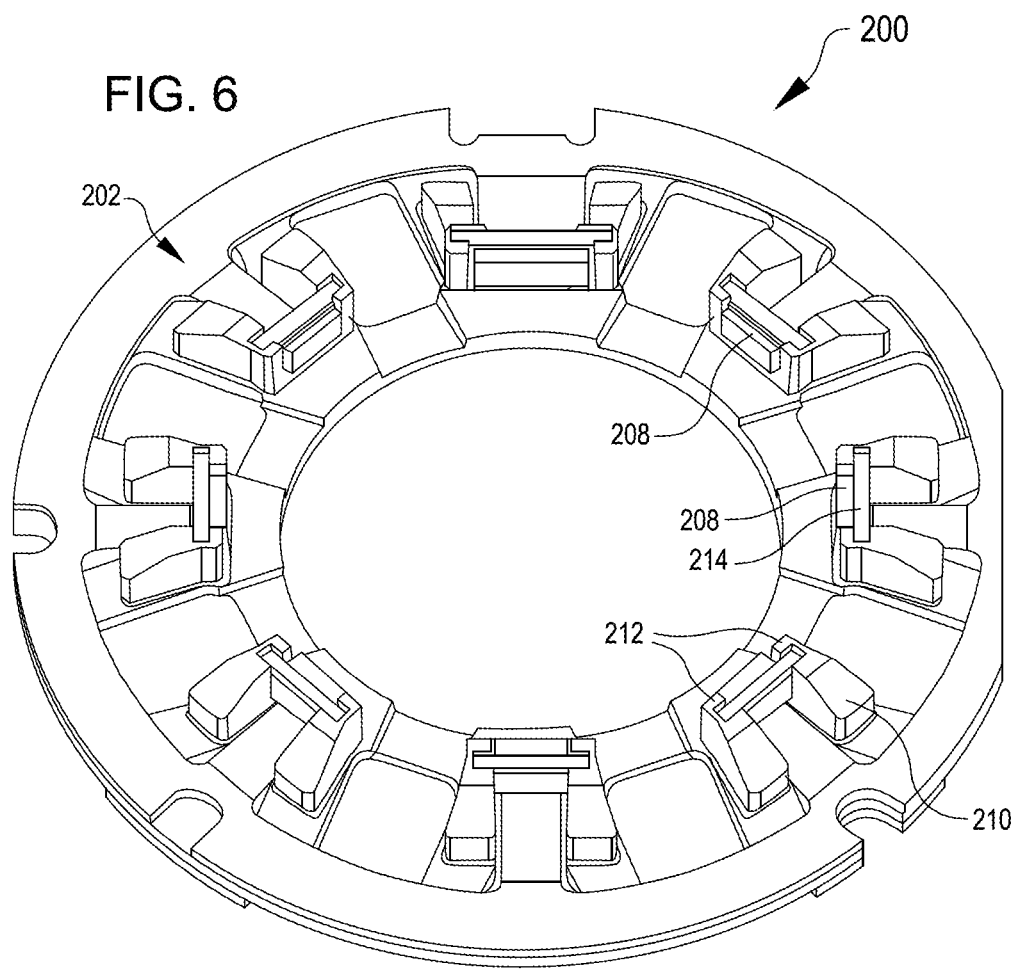
FIG. 6 is an illustration of an embodiment of a Hall Sensor assembly for the blood pump of FIG. 3.

FIG. 6 shows a Hall Sensor assembly 200 for the blood pump assembly 14, in accordance with many embodiments. The Hall Sensor assembly 200 includes a printed circuit board (PCB) 202 and individual Hall Effect sensors 208 supported by the printed circuit board 202. Eight axisymmetric Hall Effect sensors 208 are placed in a rigid, plastic mechanical carrier 210 and the PCB 202 is placed onto the mechanical carrier 210. The mechanical carrier 210 uses guide rails 212 to locate electrically neutral rigid PCB portions 214 attached to the top edges of the Hall Effect sensors 208 and to locate the PCB 202.

The Hall Effect sensors 208 are configured to transduce a position of the rotor 140 of the pump 100. In the illustrated embodiment, the Hall Effect sensors 208 are supported so as to be standing orthogonally relative to the PCB 202 and a longest edge of each of the Hall Effect sensors 208 is aligned to possess an orthogonal component with respect to the surface of the PCB 202. Each of the Hall Effect sensors 208 generate an output voltage, which is directly proportional to a strength of a magnetic field that is located in between at least one of the pole pieces 123a-123f and the permanent magnet 141. The voltage output by each of the Hall Effect sensors 208 is received by the control electronics 130, which processes the sensor output voltages to determine the position and orientation of the rotor 140. The determined position and orientation of the rotor 140 is used to determine if the rotor 140 is not at its intended position for the operation of the pump 100. For example, a position of the rotor 140 and/or the permanent magnet 141 may be adjusted, for example, the rotor 140 or the permanent magnet 141 may be pushed or pulled towards a center of the blood flow conduit 103 or towards a center of the stator 120. The determined position of the rotor 140 can also be used to determine rotor eccentricity or a target rotor eccentricity, which can be used as described herein to estimate flow rate of blood pumped by the blood pump assembly 100.

Figure 7:
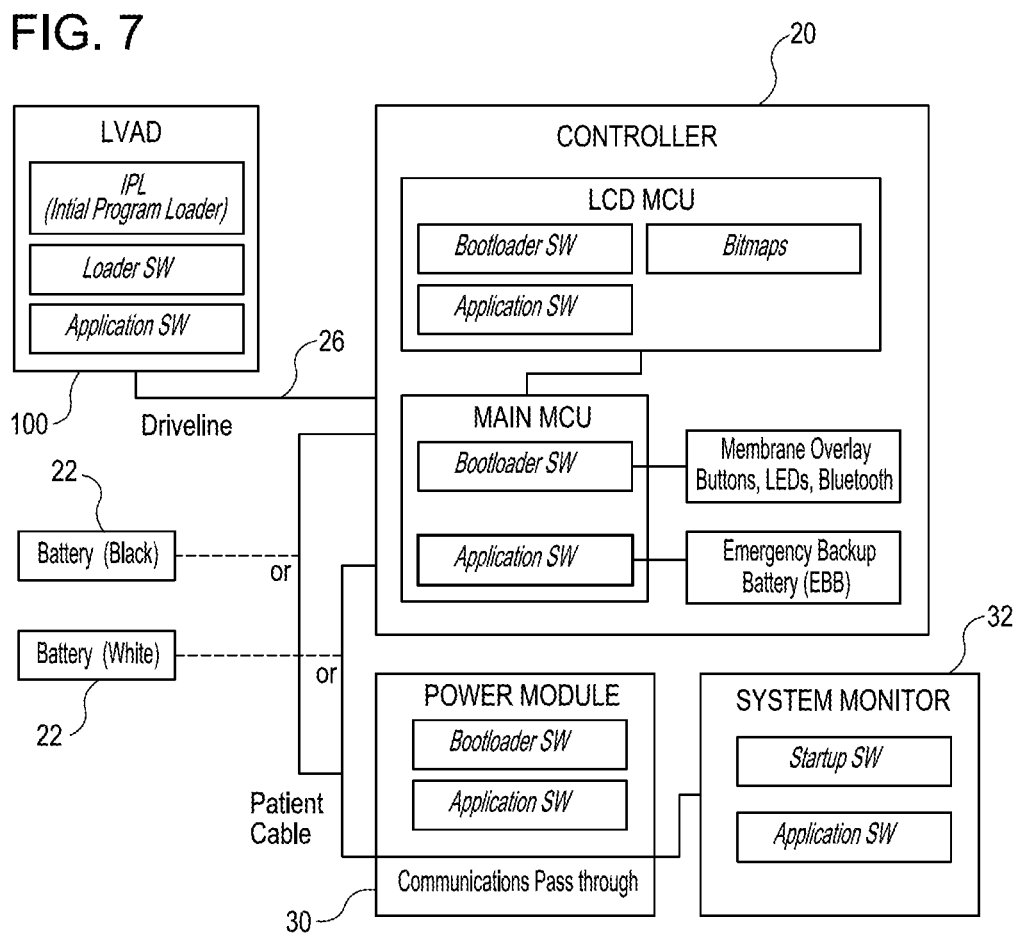
FIG. 7 is a schematic diagram of a control system architecture of the mechanical support system of FIG. 1.

FIG. 7 is a schematic diagram of a control system architecture of the mechanical support system of FIG. 1. The driveline 26 couples the implanted blood pump assembly 100 to the external system controller 20, which monitors system operation via various software applications. The blood pump assembly 100 itself also includes several software applications that are executable by the on board electronics 130 (e.g., processors) for various functions, such as to control radial levitation and/or drive of the rotor of the pump assembly 100 during operation. The external system controller 20 can in turn be coupled to batteries 22 or a power module 30 that connect to an AC electrical outlet. The external system controller 20 can also include an emergency backup battery (EBB) to power the system (e.g., when the batteries 22 are depleted) and a membrane overlay, including Bluetooth capabilities for wireless data communication. An external computer having a system monitor 32 that is configurable by an operator, such as clinician or patient, may further be coupled to the circulatory support system for configuring the external system controller 20, implanted blood pump assembly 100, and/or patient specific parameters, updating software on the external system controller 20 and/or implanted blood pump assembly 100, monitoring system operation, and/or as a conduit for system inputs or outputs.

Impeller Position Based Flow Estimation

Figure 8:
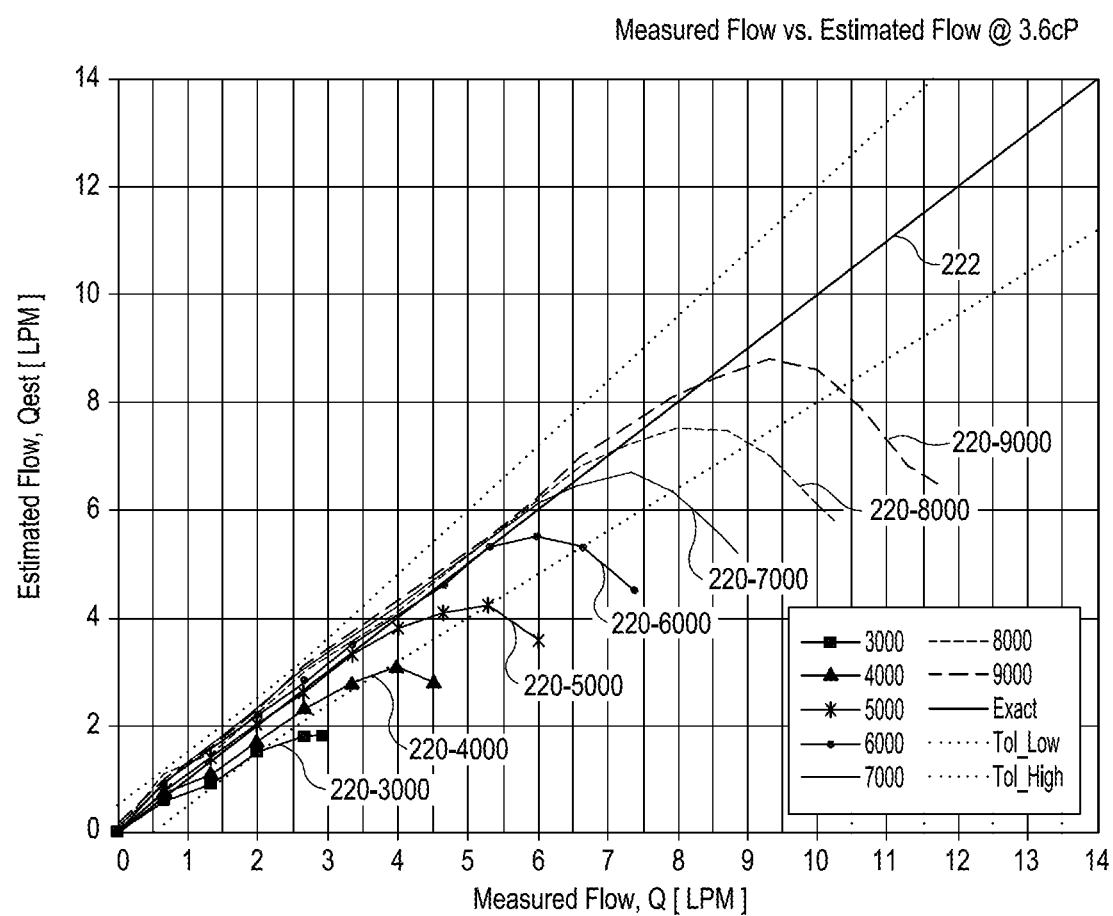
FIG. 8 graphically illustrates deviations between flow rates estimated based on power consumption and measured flow rates for an example blood pump.

FIG. 8 graphically illustrates example deviations between measured flow rate for an example blood pump and flow rates (220-3000, 220-4000, 220-5000, 220-6000, 220-7000, 220-8000, 220-9000) estimated for the example blood pump based on power consumption and rotor rotation rate for a number of different impeller rotation rates. Ideally, the estimated flow rate would correspond to an exact estimated flow 222 that is equal to the measured flow rate. For a range of impeller rotation rates, however, there is a range of measured flow rates in which, for a particular impeller rotation rate and a particular blood pump, the same power consumption magnitude is used to produce two different actual measure flow rates. For example, for the estimated flow rate curve 220-9000 for an impeller rotation rate of 9000 rpm, the same estimated flow rate of 8.0 L/min corresponds to two different actual measured flow rates of about 7.8 L/min and 10.6 L/min. Moreover, for all actual measured flow rates above 9.3 L/min for an impeller rotation rate of 9000 rpm, the actual power consumption drops with increasing flow rate thereby resulting in increasing magnitude of error between the estimate flow rate 220-9000 and the exact estimated flow 222. Such a doubled value characteristic can also be seen in the data displayed in FIG. 8 for impeller rotation rates of 4000 rpm to 9000 rpm. Accordingly, estimating flow rate based only on impeller rotation rate and power consumption can result in significant relative error for actual pump flow rates at the high end of the actual flow rate range. In many embodiments, one or more additional flow rate related parameters are employed to produce more accurate flow rate estimates. As described herein, in many embodiments, estimated flow rate for at least some ranges of flow rate is based on an actual or target impeller transverse eccentricity.

Figure 9:
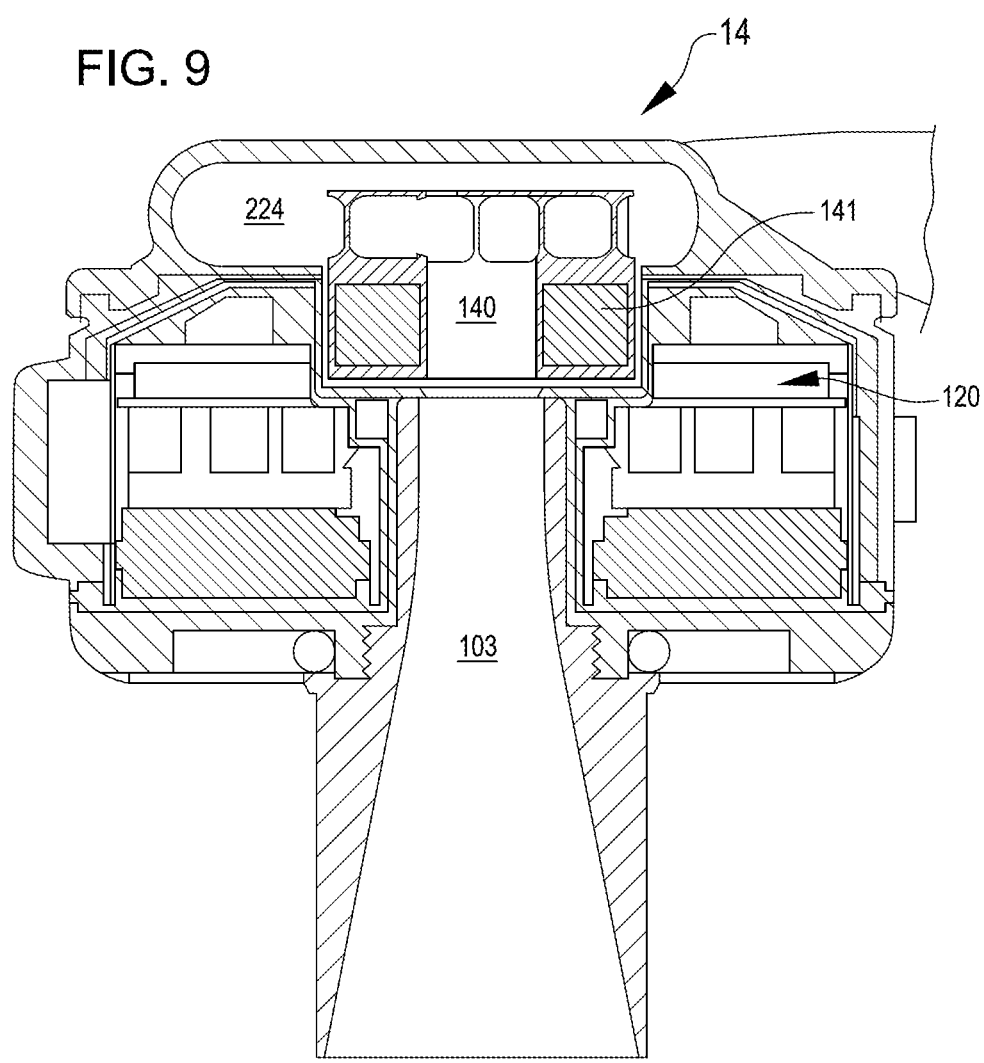
FIG. 9 shows a cross-sectional view of a centrifugal blood pump, in accordance with many embodiments.
Figure 10:
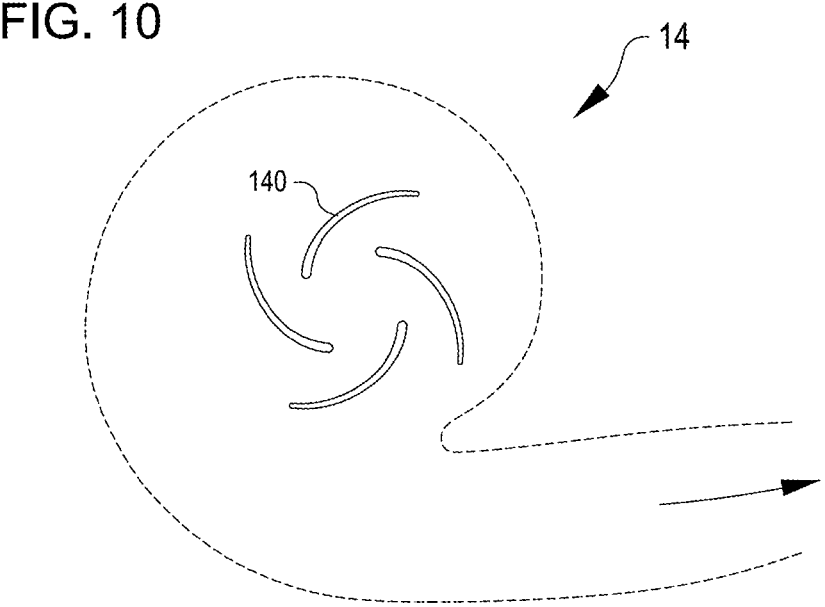
FIG. 10 schematically illustrates impeller eccentricity, in accordance with many embodiments.

FIG. 9 shows a cross-sectional view of the centrifugal blood pump 14, in accordance with many embodiments. As described herein, the rotor 140 is magnetically levitated in the blood flow channel 103 via magnetic interaction between the permanent magnet 141 and the motor stator 120. The blood flows through the center of the rotor 140 and is impelled into an axially non-symmetric output chamber 224 from which the blood is output from the blood pump 14 via the outlet 105 shown in FIG. 4. As a result of the transverse momentum imparted to the blood flow by the rotor 140, the rotor is subjected to a transverse force that is reacted via magnetic interaction between the permanent magnet 141 and the motor stator 120. While the motor stator 120 can be controlled so as to keep the rotor 140 centered within the blood flow channel, the power consumption of the blood pump 14 can be reduced by allowing the position of the rotor 140 to deviate from being centered in the blood flow channel 103. Moreover, as described herein, minimizing the power consumption of the blood pump 14 over a range of operating conditions (e.g., impeller rotation rate, flow rate) results in target impeller eccentricity that varies as a function of flow rate over at least a range of operating conditions so as to enable use of the target impeller eccentricity as a parameter from which to estimate flow rate. FIG. 10 schematically illustrates impeller eccentricity that occurs in the presence of transverse force being applied to the rotor 140 and minimization of the power consumption of the blood pump 14.

Figure 11:
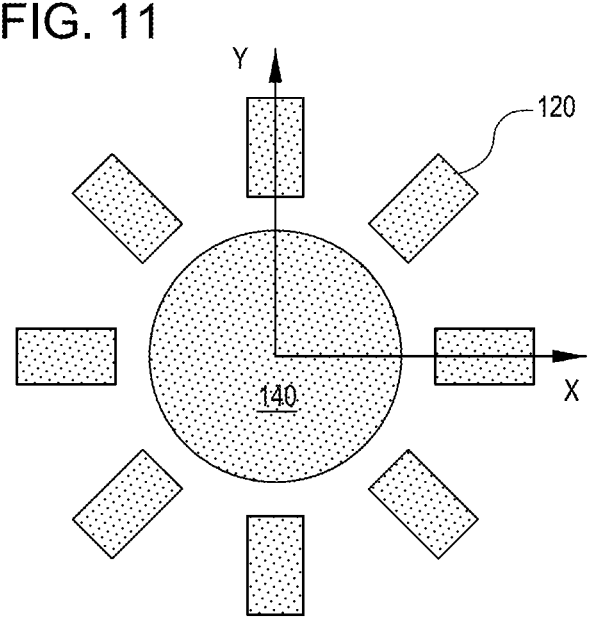
FIG. 11 shows a simplified schematic view of an impeller levitated via a motor stator, in accordance with many embodiments.

FIG. 11 shows a simplified cross-sectional schematic view of the rotor 140 levitated via the motor stator 120. The output from the Hall sensors 208 is processed to determine the transverse position of the rotor 140 in both X and Y directions. The displacement of the rotor 140 from a centered reference position in each of the X and Y directions can be combined to generate a total vector sum eccentricity of the rotor 140 from the centered reference position.

Figure 12:
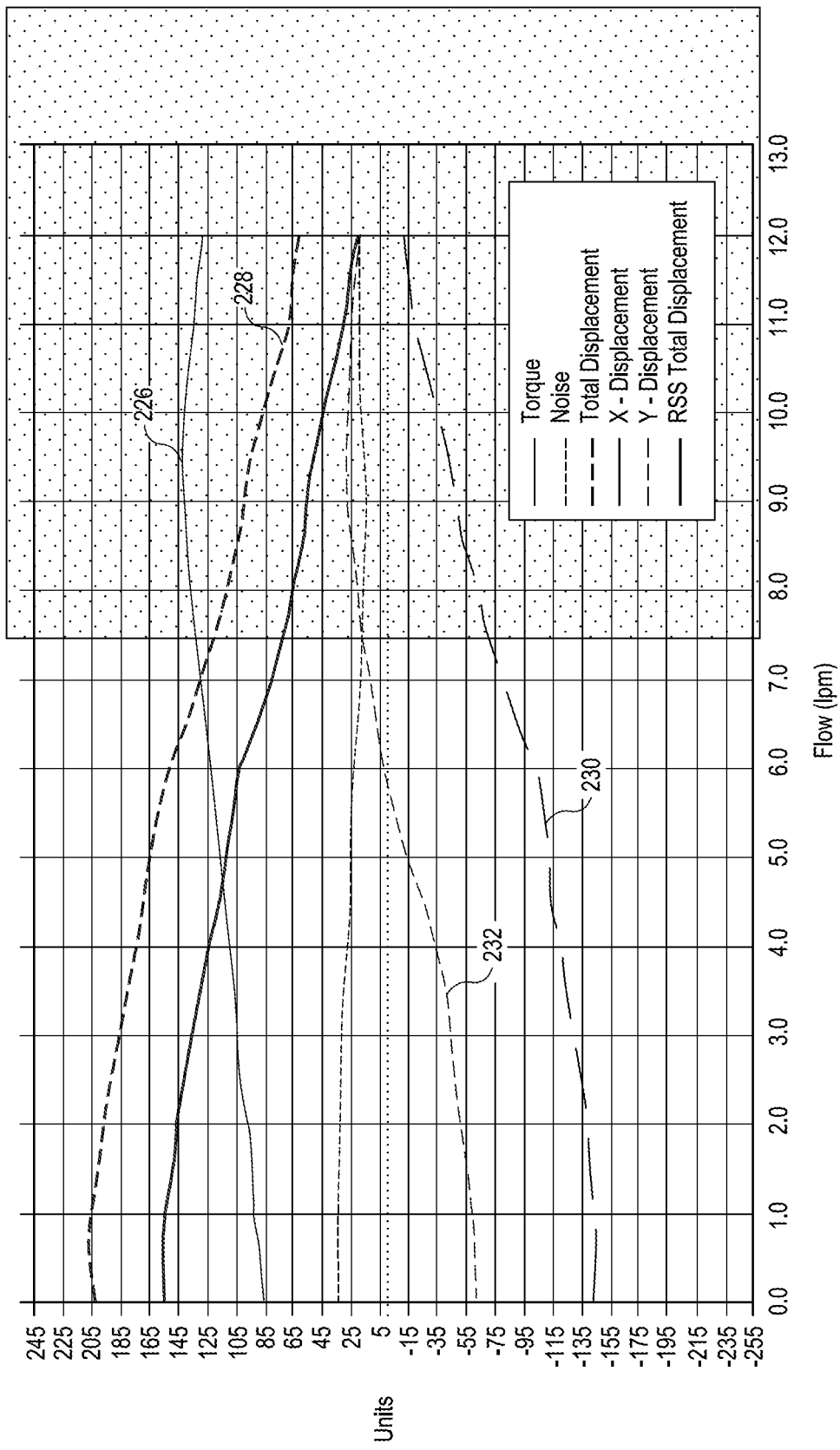
FIG. 12 is a plot showing observed correlations between measured flow rate and pump parameters including torque and impeller eccentricity values.

FIG. 12 is a plot showing observed correlations between measured flow rate and pump parameters including torque and impeller eccentricity values for an example pump operated at 9000 rpm. As can be seen, the torque 226 increases with flow up to a flow rate of about 9.5 L/min and then drops thereafter. The torque 226 is proportional to drive current and is double valued in the shaded range of flow rate greater than 7.5 L/min. Accordingly, estimation of pump flow rate based on the torque 226 for flow rates greater than about 9.5 L/min may produce increasingly more relative error between the estimated flow rate and the actual flow rate. In contrast, the total rotor eccentricity 228, which is the vector sum of the X-direction rotor eccentricity 230 and the Y-direction rotor eccentricity 232, is single valued in the shaded range of flow rate greater than 7.5 L/min, and can therefore be employed to estimate flow rate at least in some or all of the shaded flow rate range of greater than 7.5 L/min.

Figure 13:
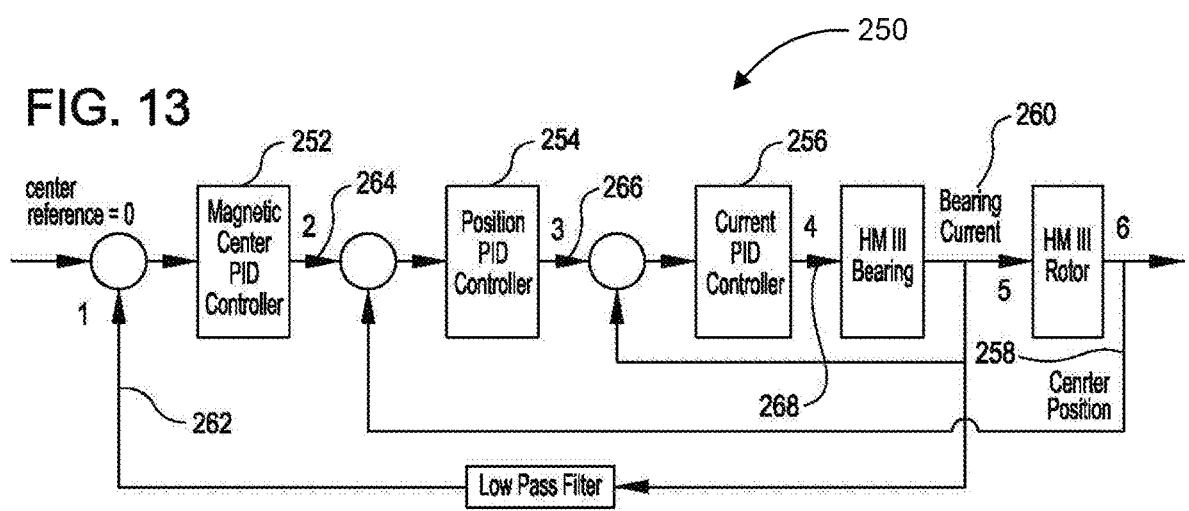
FIG. 13 is a simplified schematic illustration of a control architecture for generating current applied to levitation coils of a blood pump to transversely levitate an impeller, in accordance with many embodiments.

As described herein, the blood pump 14 magnetically levitates and rotates the rotor 140. Driving current is applied to the drive coils 125. Current for levitating the rotor is applied to the levitation coils 127. FIG. 13 is a simplified schematic illustration of a bearing current controller 250 for generating current applied to the levitation coils 127 of the blood pump 14 to transversely levitate the rotor 140, in accordance with many embodiments. The bearing current controller 250 includes a magnetic center proportional-integral-derivative (PID) controller 252, a position PID controller 254, and a current PID controller 256. The current generated is applied to the levitation coils 127 to controllably levitate the rotor 140. The resulting position of the rotor 140 (signal 258) is determined from the output of the Hall sensors 208. The bearing current controller 250 employs a three-level cascaded PID control method. The ultimate feedback signal is the bearing current 260 therefore the bearing current controller 250 is configured to minimize bearing current to reduce power consumption of the blood pump 14.

At different flow rates, the resulting bearing current is different reflecting the different forces on the rotor from the impelled blood. In the described embodiment, there are two bearing currents because there are two separate bearing coils on the stator 120 (two for each direction). A Park transformation is applied to change the coordinates from stator referenced directions (X and Y) to the rotor referenced directions (d and q directions). Two separate bearing current controllers 250 are used to control the current applied to the levitation coils 127—one for each of the d and q directions. The direction d is aligned along the rotor N-S dimension. The direction q is perpendicular to the direction d. The directions d and q define a plane perpendicular to the direction of flow through the center of the rotor 140.

The magnetic center PID controller 252 generates reference signals for the position PID controller 254 defining a target off-center position for the rotor (in the d-q coordinate system) to minimize bearing current. The position PID controller 254 generates reference signals for the bearing current in the d-q coordinate system. The current PID controller 254 calculates the bearing current in the d-q coordinate system and then applies an inverse Park transformation to generate current output for application to the levitation coils 127 to control levitation of the rotor 140 in each of the two separate directions (X and Y).

Signals 262, 264, 266, 268, 260, 258 generated by the bearing current controller 250 were studied for possible use in estimating flow rate. Because of the cascaded control structure employed, the signals 262, 264, 266, 268, 260, 258 generated by the bearing current controller 250 show similar trend of changes when flow rate is changed, although the trend direction may be reversed because of the negative feedback sign change. Signals 266, 268, 260, 258 show high run-to-run variation and noise-to-signal ratio is high due to the bearing current and center position feedback signals have significant disturbance induced from the fluid field. Signal 262 and signal 264 are more stable because the feedback signal is the bearing current after a low pass filter. Signal 264 is the target reference rotor center position, which is even more stable than signal 262, because the gain in the magnetic center PID controller 252 is zero. The magnetic center PID controller 252 imposes 20 dB attenuation from DC up to a frequency. Accordingly, the target reference rotor center position signal 264, which defines the target off-center position for the rotor (in the d-q coordinate system) to minimize bearing current, provides a suitable signal that can be processed to estimate flow rate of the blood pump. For example, each of the target reference rotor center signals 264 from the two bearing current controllers 250 (one for the X-direction levitation current and one for the Y-direction levitation current) can be combined to calculate a target reference rotor center value corresponding to a total target eccentric distance of the target off-center position for the rotor from the center of the blood flow channel of the blood pump.

Figure 14:
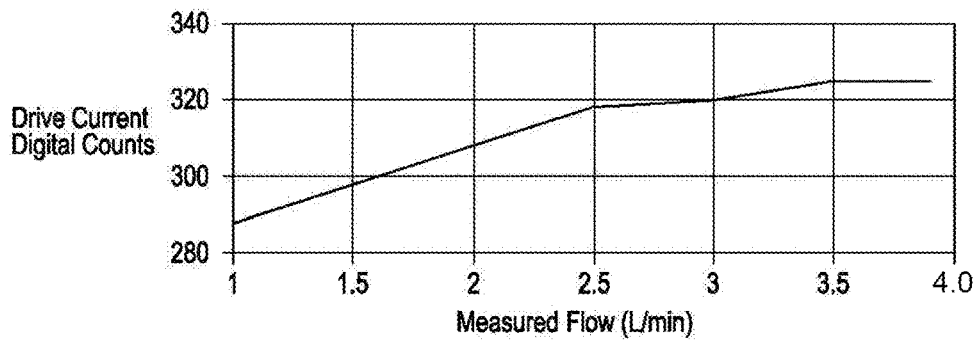
FIG. 14 is a plot showing an observed correlation between measured flow and impeller drive current for an example blood pump operated at 3000 rpm.

FIG. 14 is a plot showing an observed correlation between measured flow and impeller drive current for an example blood pump operated at 3000 rpm. As illustrated in FIG. 14, for measured flow rates from 1 L/min to 2.5 L/min, the corresponding drive current used to rotate the impeller shows a substantially linear increase from about 288 counts to about 318 counts. Above 2.5 L/min, the increase in drive current with increased measured flow rate diminishes down to no significant increase in drive current for measured flow rate between 3.5 L/min and 4.0 L/min. Accordingly, estimated flow rate based only on drive current for impeller rotation rate of 3000 rpm may deviate increasingly from actual flow rate for flow rates above 2.5 L/min.

Figure 15:
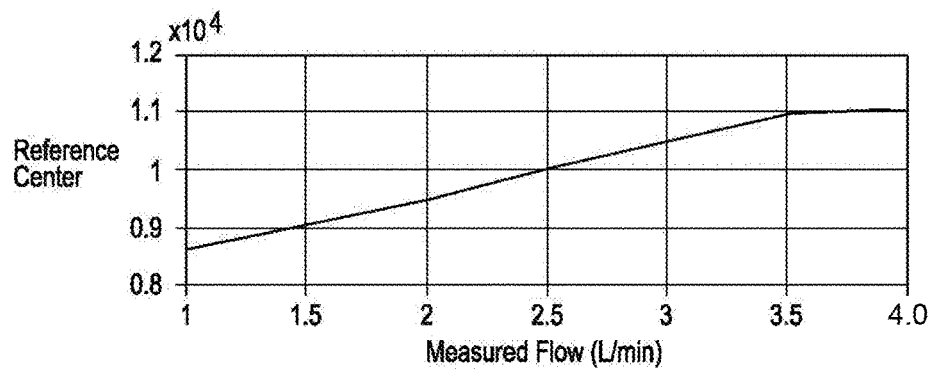
FIG. 15 is a plot showing an observed correlation between measured flow and target transverse eccentricity of the impeller of the example blood pump of FIG. 14 operated at 3000 rpm.

FIG. 15 is a plot showing an observed correlation between measured flow and the target reference center value of the example blood pump of FIG. 14 operated at 3000 rpm. As illustrated in FIG. 15, for measured flow rates from 1 L/min to 3.5 L/min, the corresponding target reference center value shows a substantially linear increase. Therefore, the target reference center value can be used to increase the accuracy of estimated flow rate, at least in the 2.5 L/min to 3.5 L/min range for the example blood pump of FIG. 14 operated at 3000 rpm.

Figure 16:
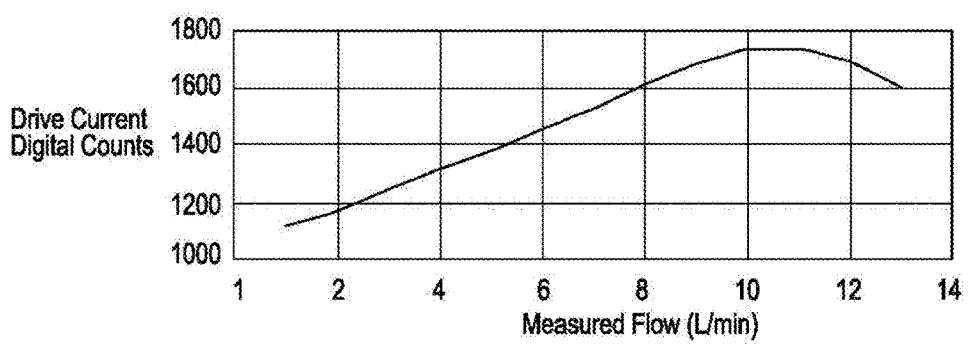
FIG. 16 is a plot showing an observed correlation between measured flow and impeller drive current for the example blood pump of FIG. 14 operated at 9000 rpm.

FIG. 16 is a plot showing an observed correlation between measured flow and impeller drive current for the example blood pump of FIG. 14 operated at 9000 rpm. As illustrated in FIG. 16, for measured flow rates from about 1.5 L/min to about 10.0 L/min, the corresponding drive current used to rotate the impeller shows a substantially linear increase from about 1120 counts to about 1750 counts. From about 10.0 L/min to about 11.0 L/min, the corresponding drive current used to rotate the impeller shows no significant change. Above 11.0 L/min, the corresponding drive current used to rotate the impeller drops down to about 1600 counts at about 13.0 L/min flow rate. Accordingly, estimated flow rate based only on drive current for impeller rotation rate of 9000 rpm may deviate increasingly from actual flow rate for flow rates above 10.0 L/min.

Figure 17:
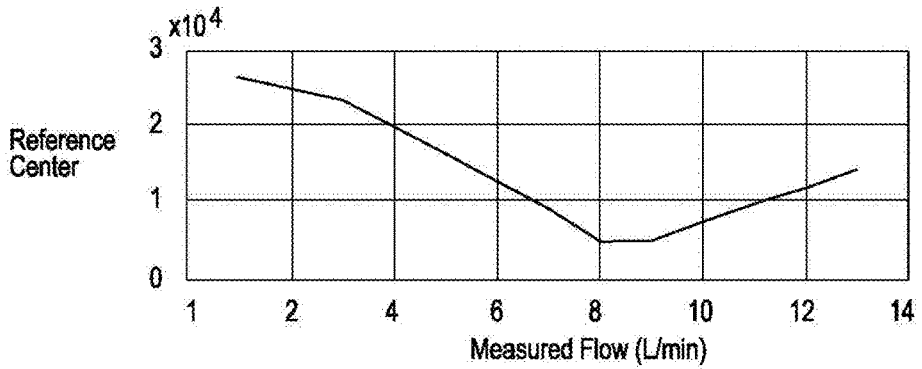
FIG. 17 is a plot showing an observed correlation between measured flow and target transverse eccentricity of the impeller of the example blood pump of FIG. 14 operated at 9000 rpm.

FIG. 17 is a plot showing an observed correlation between measured flow and the target reference center value of the example blood pump of FIG. 14 operated at 9000 rpm. As illustrated in FIG. 17, for measured flow rates from 1 L/min to 8.0 L/min, the corresponding target reference center value shows a substantially linear decrease. From 8.0 L/min to 9.0 L/min flow rate, the corresponding target reference center value shows no significant change. Above 9.0 L/min flow rate, the corresponding target reference center value exhibits a substantially linear increase with increasing flow rate. Therefore, the target reference center value can be used to increase the accuracy of estimated flow rate, at least in the 9.0 L/min and higher range for the example blood pump of FIG. 14 operated at 9000 rpm.

An interesting observation from FIG. 15 and FIG. 17 is that the target reference center value is correlated with flow rate. Although the target reference center value also has bell curve shape meaning it also has double value problem for use in estimating flow rate, its double value range is different from the double value range of the driving current. Accordingly, one method that can be used to overcome the estimation error arising from the double valued nature of the driving current and flow rate correlation is to combine the driving current with the target reference center to predict the flow rate, for example, switching from driving current to the target reference center when driving current is in the double value range.

There are at least two approaches for selecting when to switch between estimating flow rate based on driving current and estimating flow rate based on target reference center. One method selects a single flow rate value to switch for each particular rotor rotational rate. For example, when driving current is higher than 1600 counts in FIG. 16, driving current is in the double value range, so the flow can be estimated based on target reference center instead of drive current when the driving current is higher than 1600 counts.

Figure 18:
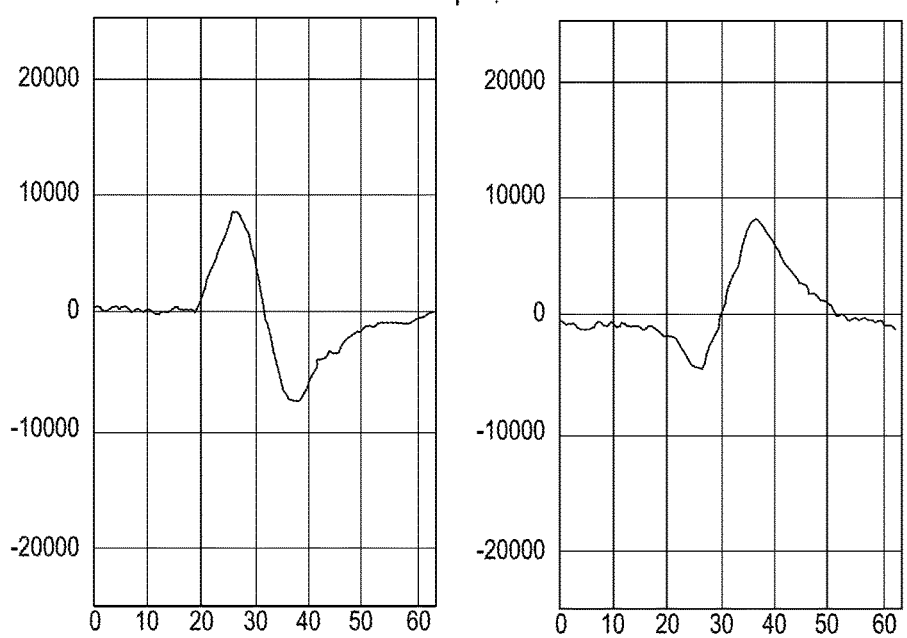
FIG. 18 is a plot showing bearing current variations during pulsatile mode operation of the example blood pump of FIG. 14 operated at a nominal 7000 rpm and 10 L/min.
Figure 19:
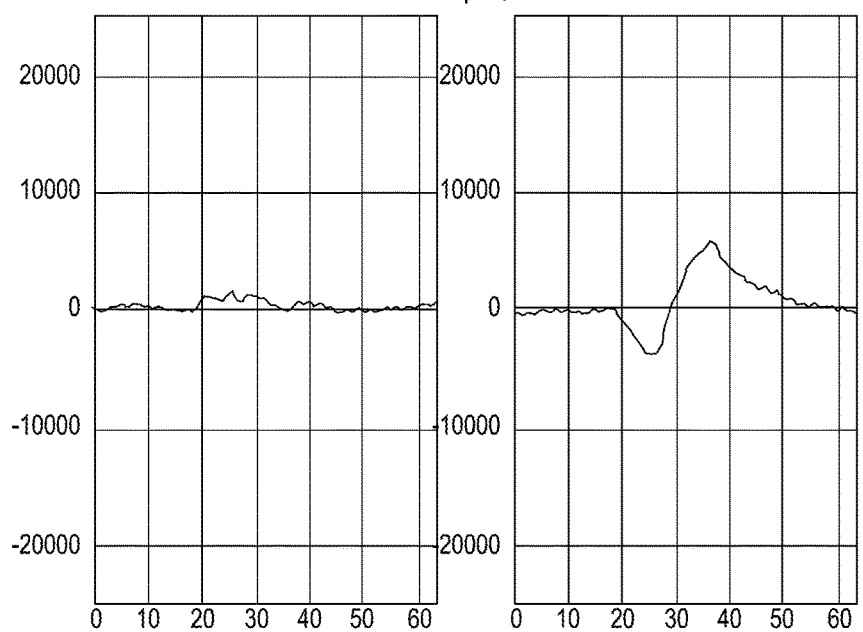
FIG. 19 is a plot showing bearing current variations during pulsatile mode operation of the example blood pump of FIG. 14 operated at a nominal 7000 rpm and 7 L/min.
Figure 21:
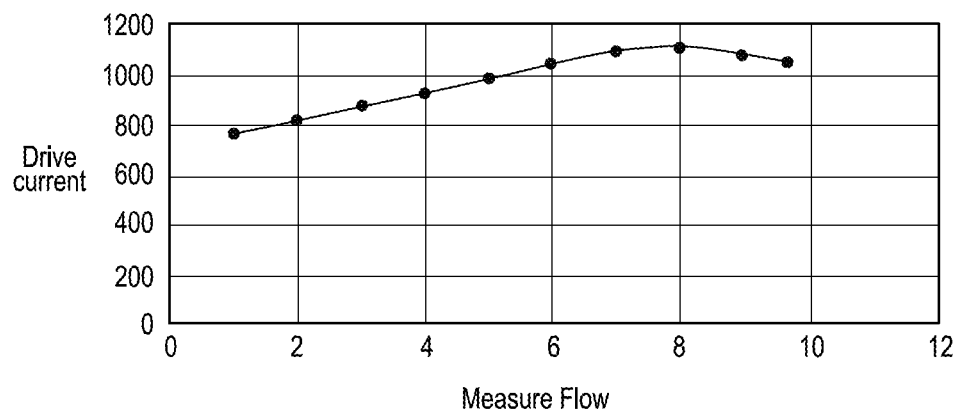
FIG. 21 is a plot showing an observed correlation between measured flow and impeller drive current for the example blood pump of FIG. 14 operated at 7000 rpm.
Figure 22:
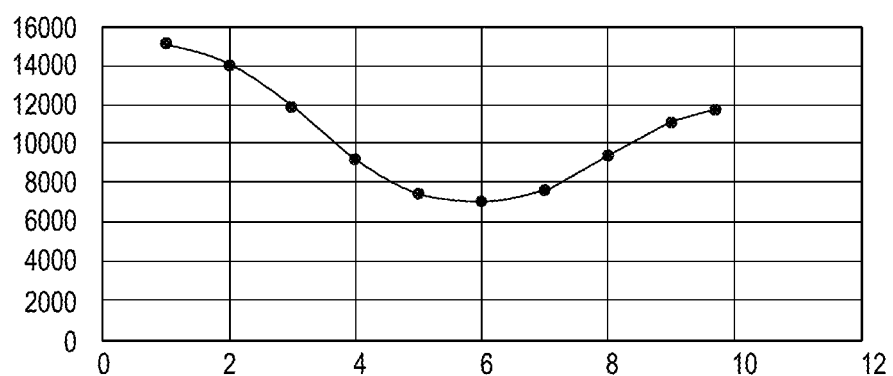
FIG. 22 is a plot showing an observed correlation between measured flow and target transverse eccentricity of the impeller of the example blood pump of FIG. 14 operated at 7000 rpm.

A second method for determining what flow rate to switch between estimating flow rate based on driving current and estimating flow rate based on target reference center is based on how the bearing current varies in response to a pulsatile variation in the rotation rate of the rotor. The merit of the second method is that no calibration variable is involved in the second method's algorithm based switching, which may therefore be more robust in implementation. During pulsatile mode operation of the blood pump, the rotor rotational rate is periodically varied to simulate natural blood pulse. On a periodic basis, the rotor rotational rate is temporarily reduced from the current nominal rotational rate, then temporarily increased from the reduced rate to a rate greater than the current nominal rotation rate, and then reduced back down to the current nominal rotational rate. During each of these pulsatile rotation rate variations, a transition is also observed in bearing current. When bearing current is decomposed into d-q coordinates, it is found that the pulsatile transition of the bearing current changes with flow rate. FIGS. 18 through 20 show the bearing currents filtered by the low pass filter and decomposed into d-q coordinates for different flow rates for a rotor rotation rate of 7000 rpm. The left subfigure is for the d axis, and right for the q axis. The d axis bearing current transition goes up then down at 10 L/min, and goes down then up at 3 L/min. The change in direction of the bearing current transition indicates that 10 L/min flow rate and 3 L/min flow rate are on different sides of the target reference center bell curve. FIG. 21 is a plot showing an observed correlation between measured flow and impeller drive current for the example blood pump of FIG. 14 operated at 7000 rpm. FIG. 22 is a plot showing an observed correlation between measured flow and target reference center of the impeller of the example blood pump of FIG. 14 operated at 7000 rpm. As shown in FIG. 22, the target reference center value bottoms at 6 L/min. Therefore the slope of the target reference center curve with flow is reversed at 6 L/min, which causes the difference in pulsatile transition of the related rotor levitation current.

This pulsatile transition change in bearing current can be used to set an estimation parameter having either a value of 0.0 or 1.0 based on whether the shape of the pulsatile transition change in bearing current indicates that the current nominal flow rate is lower or higher than the flow rate at which the target reference center curve bottoms. The estimation parameter can then be used to switch between estimating flow rate based on drive current when the flow rate is below the flow rate at which the target reference center curve bottoms and estimating flow rate based on target reference center value when the flow rate is above the flow rate at which the target reference center bottoms. For example, FIGS. 21 and 22 show that for an example pump operated at 7000 rpm, driving current is a good estimator until about 7 L/min. Based on the pulsatile transition change in bearing current signature, the estimation parameter can be set to 1.0 at 7 L/min and higher so that the target reference center value can be used to estimate flow rate for flow rates of 7 L/min or higher.

Figure 23:
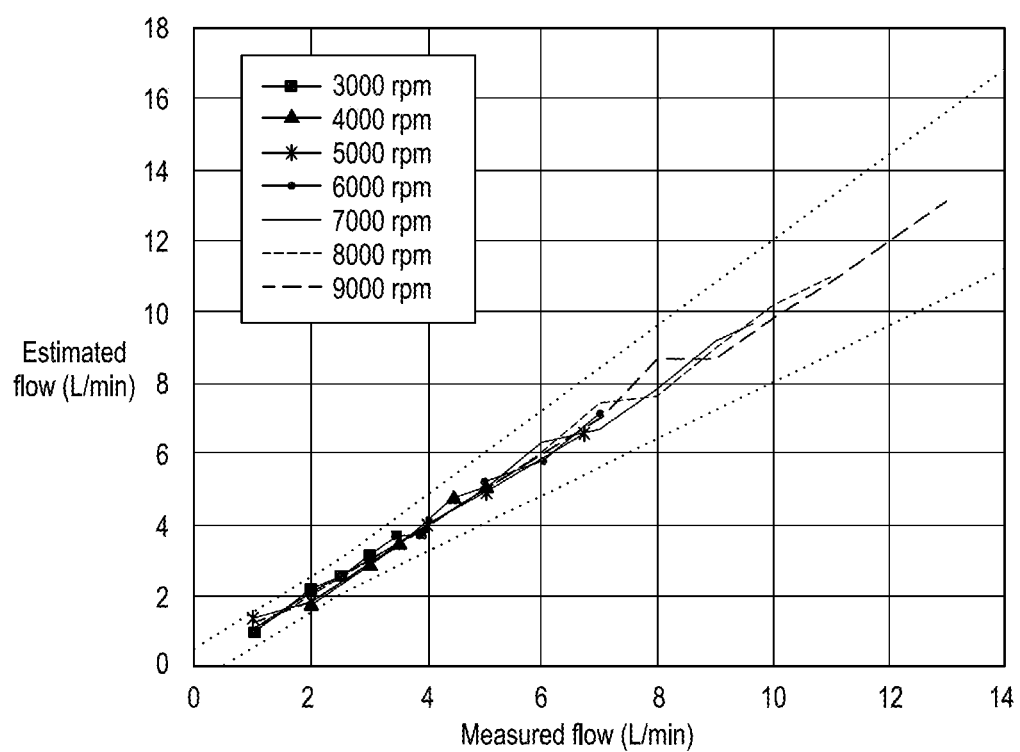
FIG. 23 graphically illustrates deviations between flow rates estimated based on power consumption and target impeller eccentricity and measured flow rates for the example blood pump of FIG. 14, in accordance with many embodiments.

Calibration can also be done to fit the target reference center signal with the flow rate. To avoid switching noise when operating close to the switching flow rate, a weighing method can be used to put less weight on the target reference center signal when the pulsatile transition change in the bearing current indicates a flow rate corresponding to approximately the bottom of the target reference signal, and gradually add more weight to reference center signal at higher flow rate. The accuracy of this weighing method is illustrated in FIG. 23, which graphically illustrates deviations between the resulting measured flow rate and actual flow rate for the example blood pump of FIG. 14.

Other suitable approaches for increasing the accuracy of flow rate estimation using parameters related to rotor levitation are also possible. For example, any suitable existing curve fitting techniques can be used to estimate flow rate based on any suitable combination of rotor rotation rate, drive current, and target reference center. Also, two or more different curve fits can be used to cover the entire range of flow rates. For example, one curve fit can be used to estimate flow rate at the low range of flow rates where flow rate is primarily a function of driving current, a second curve fit can be used at the high range of flow rates based on target reference center, and a third curve fit can be used at the mid-range of flow rates based on both driving current and target flow rate. Other bearing current related parameters can also be used. For example, the bearing current can be controlled to keep the rotor centered in the blood flow channel and the variation in the bearing current, which will be greater if the rotor is kept centered, can be used as another parameter in addition to rotor driving current to estimate flow rate.

Impeller Position Based Pump Pressure Differential Estimation

One of skill in the art would appreciate that the parameters related to impeller position described herein (e.g., bearing current, off-center position for the impeller to minimize bearing current) can be used alone or in combination to estimate pressure differential across the impeller (i.e., difference in pressure on the output side of the impeller to pressure on the input side of the impeller) in addition to or instead of estimating flow. For example, in many embodiments of the centrifugal blood pump 14, the impeller eccentricity for minimum bearing current appears to be solely or mostly dependent upon the pressure differential across the impeller. As a result, the pressure differential across the impeller can be estimated using a suitable function of the parameters related to impeller position described herein. Also, any suitable additional operational parameter of the blood pump, such as pump rotational speed, impeller drive current, and/or estimated blood flow through the pump, can be used alone or in any suitable combination in addition to the parameters related to impeller position described herein to estimate the pressure differential across the impeller. Moreover, one of skill would appreciate that the pressure differential across the impeller can be derived from the flow rate of blood through the blood pump and vice versa. The resulting estimated pressure differential can be used in any suitable way, including as a parameter on which operation of the pump is based to produce desired pressure differential across the pump suitable for particular patient physiological conditions and/or to detect and react to adverse pump conditions.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A blood circulation assist system, comprising:
   a blood pump comprising an impeller disposed within a blood flow channel of the blood pump and a motor stator operable to magnetically rotate the impeller, the impeller having an impeller axis of rotation around which the impeller is rotated, the motor stator being further operable to magnetically levitate the impeller within the blood flow channel transverse to the impeller axis of rotation; and
   a controller operatively coupled with the blood pump, the controller being configured to:
      determine an impeller rotational speed for the impeller;
      determine at least one impeller transverse position parameter based on at least one of (1) an amount of a bearing current that is used to levitate the impeller transverse to the impeller axis of rotation, and (2) a position of the impeller within the blood flow channel transverse to the impeller axis of rotation; and
      estimate a flow rate of blood through the blood pump based on the impeller rotational speed and the at least one impeller transverse position parameter.

2. The blood circulation assist system of claim 1, wherein the controller is configured to:
   determine an amount of a drive current used to rotate the impeller; and
   estimate the flow rate based on the impeller rotational speed and the at least one impeller transverse position parameter when the amount of the drive current is above a drive current threshold.

3. The blood circulation assist system of claim 2, wherein the drive current threshold varies based on the impeller rotational speed.

4. The blood circulation assist system of claim 2, wherein the drive current threshold is based on characteristics of variation in the amount of bearing current used to levitate the impeller transverse to the impeller axis of rotation in response to variation in the impeller rotational speed.

5. The blood circulation assist system of claim 4, wherein the drive current threshold is selected such that the amount of bearing current used to levitate the impeller transverse to the impeller axis increases in response to a decrease in the impeller rotational speed for drive currents above the drive current threshold.

6. The blood circulation assist system of claim 1, wherein the controller is configured to:
   determine an amount of a drive current used to rotate the impeller; and
   estimate the flow rate based on the impeller rotational speed, the amount of the drive current, and the at least one impeller transverse position parameter when the amount of the drive current is within a drive current range.

7. The blood circulation assist system of claim 1, wherein the impeller impels blood centrifugally and the blood pump outputs blood in a direction transverse to the impeller axis of rotation.

8. The blood circulation assist system of claim 1, wherein the at least one impeller transverse position parameter is indicative of an amount of eccentricity of the impeller within the blood flow channel.

9. The blood circulation assist system of claim 1, further comprising at least one sensor generating output indicative of the position of the impeller within the blood flow channel transverse to the impeller axis of rotation.

10. The blood circulation system of claim 9, wherein the at least one sensor comprises a plurality of Hall sensors generating output indicative of the position of the impeller within the blood flow channel transverse to the impeller axis of rotation.

11. The blood circulation assist system of claim 1, wherein the controller is configured to control the amount of a bearing current that is used to levitate the impeller transverse to the impeller axis of rotation so as to substantially minimize power consumption of the blood pump.

12. The blood circulation assist system of claim 1, wherein the controller is configured to control eccentricity of the impeller within the blood flow channel so as to substantially minimize power consumption of the blood pump.

13. The blood circulation assist system of claim 12, wherein the flow rate is estimated based on eccentricity of the impeller within the blood flow channel.

14. A blood circulation assist system, comprising:
   a blood pump comprising an impeller and a motor stator, the impeller being disposed within a blood flow channel of the blood pump and having an impeller axis of rotation around which the impeller is rotated, the motor stator comprising drive coils and levitation coils, driving current being applied to the drive coils to rotate the impeller around the impeller axis of rotation, bearing current being applied to the levitation coils to levitate the impeller transverse to the impeller axis of rotation; and
   a controller operatively coupled with the drive coils and the levitation coils, the controller being configured to control the bearing current so as to substantially minimize power consumption of the blood pump during operation of the blood pump comprising rotation of the impeller around the impeller axis of rotation.

15. The blood circulation assist system of claim 14, wherein the controller comprises a bearing current controller that generates the bearing current based on a measured position of the impeller transverse to the impeller axis of rotation.

16. The blood circulation assist system of claim 15, wherein the blood pump comprises Hall sensors that generate output indicative of the measured position of the impeller transverse to the impeller axis of rotation.

17. The blood circulation assist system of claim 15, wherein the bearing current controller uses the bearing current as a feedback signal.

18. The blood circulation assist system of claim 15, wherein the bearing current controller employs a three-level cascaded proportional-integral-derivative (PID) control method in which the measured position of the impeller transvers to the impeller axis of rotation and the bearing current are used as feedback signals.

19. The blood circulation assist system of claim 15, wherein the bearing current controller is configured to control the position of the impeller transverse to the impeller axis in each of two separate directions.

* * * * *